(12) United States Patent
Kim et al.

(10) Patent No.: US 11,337,419 B2
(45) Date of Patent: *May 24, 2022

(54) METHOD FOR LYOPHILIZING EXOSOME

(71) Applicant: ExoCoBio Inc., Seoul (KR)

(72) Inventors: Kwang Il Kim, Goyang-si (KR);
Byong Seung Cho, Gunpo-si (KR);
Yong Weon Yi, Seoul (KR)

(73) Assignee: ExoCoBio Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,258

(22) Filed: Jun. 26, 2020

(65) Prior Publication Data
US 2020/0329697 A1 Oct. 22, 2020

Related U.S. Application Data

(63) Continuation of application No. PCT/KR2019/008832, filed on Jul. 17, 2019.

(30) Foreign Application Priority Data

Jul. 28, 2018 (KR) ........................ 10-2018-0088230

(51) Int. Cl.
A01N 1/02 (2006.01)
A61K 8/34 (2006.01)
A61K 8/44 (2006.01)
A61K 8/60 (2006.01)
A61K 8/64 (2006.01)
A61K 8/67 (2006.01)
A61K 8/73 (2006.01)
A61K 9/19 (2006.01)
A61K 47/26 (2006.01)
A61K 8/72 (2006.01)
A61K 9/00 (2006.01)
A61Q 19/00 (2006.01)

(52) U.S. Cl.
CPC ......... A01N 1/0221 (2013.01); A01N 1/0284 (2013.01); A61K 8/345 (2013.01); A61K 8/447 (2013.01); A61K 8/60 (2013.01); A61K 8/606 (2013.01); A61K 8/64 (2013.01); A61K 8/671 (2013.01); A61K 8/676 (2013.01); A61K 8/735 (2013.01); A61K 9/19 (2013.01); A61K 47/26 (2013.01); A61K 8/72 (2013.01); A61K 9/0019 (2013.01); A61K 2800/84 (2013.01); A61Q 19/00 (2013.01)

(58) Field of Classification Search
None
See application file for complete search history.

(56) References Cited

U.S. PATENT DOCUMENTS 9,180,098 B2 11/2015 Hafner et al.
2010/0297231 A1 11/2010 Vehring et al.
2013/0259896 A1 10/2013 Khandke et al.
2013/0315987 A1 11/2013 Lu
2016/0367660 A1 12/2016 Hafner et al.
2017/0087187 A1 3/2017 Chang et al.
2017/0209365 A1 7/2017 Cho et al.
2018/0332951 A1 11/2018 Jang et al.
2019/0030079 A1 1/2019 Cho et al.
2020/0121722 A1 4/2020 Yi et al.
2020/0323768 A1 10/2020 Yi et al.
2021/0077379 A1 3/2021 Cho et al.

FOREIGN PATENT DOCUMENTS

| CN | 1160582 A | 10/1997 |
| CN | 106701672 A | 5/2017 |
| CN | 107006452 A | 8/2017 |
| EP | 3 199 175 | 2/2017 |
| EP | 3363817 A1 | 8/2018 |
| JP | 2012-136518 A | 7/2012 |
| JP | 2015-057383 A | 3/2015 |
| JP | 2015-78177 A | 4/2015 |
| KR | 10-2015-0108795 A | 9/2015 |
| KR | 10-1663912 B1 | 10/2016 |
| KR | 10-2017-0089404 A | 8/2017 |
| KR | 10-2018-0042217 A | 4/2018 |
| KR | 10-2019-0069301 A | 6/2019 |
| WO | 96/09037 A1 | 3/1996 |
| WO | 98/36736 A1 | 8/1998 |
| WO | 2008/040556 A1 | 4/2008 |
| WO | 2010/148337 A1 | 12/2010 |
| WO | 2016/197196 A1 | 12/2016 |
| WO | 2017/015622 A2 | 1/2017 |
| WO | 2017/020034 | 2/2017 |

(Continued)

OTHER PUBLICATIONS

Machine-assisted English translation for CN 106701672 A (Year: 2017).*
Bosch et al ("Trehalose prevents aggregation of exosomes and cryodamage", Scientific Reports (Nov. 2016)) (Year: 2016).*
International Search Report of PCT/KR2019/008832 dated Oct. 29, 2019 [PCT/ISA/210].
Ho Seong Jeon, "Improved Stability of Sterically Stabilized Liposomal Preparations by Lyophilization", Master's Thesis. Graduate School of Chung-ang University, Dec. 2000 (53 pages total).
International Search Report of PCT/KR2019/008850 dated Oct. 24, 2019 [PCT/ISA/210].

(Continued)

Primary Examiner — Sin J Lee
(74) Attorney, Agent, or Firm — Sughrue Mion, PLLC

(57) ABSTRACT

A method of lyophilizing exosomes using a cryoprotectant comprising methionine, mannitol and trehalose is disclosed. The lyophilized exosome product shows a good appearance which maintains a porous sponge shape without forming ice crystals. In addition, the lyophilized exosome product can be applied to a pharmaceutical composition, a skin external preparation and a cosmetic composition. For example, the lyophilized exosome product can be used as a solution obtained by simply mixing it with a diluent.

9 Claims, 21 Drawing Sheets

(56) References Cited

FOREIGN PATENT DOCUMENTS

| WO | 2017/122095 A1 | 7/2017 |
| WO | 2018/027075    | 2/2018 |
| WO | 2018/050872 A1 | 3/2018 |
| WO | 2018/053004 A2 | 3/2018 |
| WO | 2018/070939 A1 | 4/2018 |
| WO | 2018/078524 A1 | 5/2018 |

OTHER PUBLICATIONS

International Search Report of PCT/KR2019/005680 dated Aug. 16, 2019 [PCT/ISA/210].
NAVER Blog, "Get a regeneration care by Exosome Original Repair ampule after Fraxel treatment / Stem Cell ampule / Fraxel treatment", Oct. 22, 2015, https://blog.naver.com/restemkorea/220516198077 (8 pages total).

\* cited by examiner

METHOD FOR LYOPHILIZING EXOSOME

CROSS REFERENCE

This application is a Bypass Continuation of International Application No. PCT/KR2019/008832 filed Jul. 17, 2019, claiming priority based on Korean Patent Application No. 10-2018-0088230 filed Jul. 28, 2018, the entire contents of which are incorporated herein by reference.

TECHNICAL FIELD

The present invention relates to a method for lyophilizing exosomes, a cryoprotectant for exosomes, and a composition for lyophilizing exosomes.

Moreover, the present invention relates to lyophilized exosomes or a composition comprising lyophilized exosomes and a diluent, and applications thereof.

BACKGROUND ART

Lyophilization is a drying process in which water is removed from a water-containing sample through sublimation after the sample is frozen and placed under a vacuum. Lyophilization is used for long-term preservation of water-containing substances such as the cells or tissues of plants or animal cells as well as foods.

However, when water-containing substances are frozen, freeze-concentration occurs in which water molecules form ice crystals during freezing, resulting in uneven diffusion of solutes or contaminants in the water-containing substances. To prevent freeze-concentration in a cell, a method of adding a cryoprotectant such as dimethyl sulfoxide (DMSO), glycerol, acetamide, propylene glycol, polyethylene glycol or the like is used. The cryoprotectant increases glass transition temperature, thus preventing tissue breakdown caused by ice crystals formed during freezing and increasing the stability of the tissue.

However, in the case of eukaryotic cells, even if the cryoprotectant is used, problems arise that it is difficult to stably preserve the cells without damaging cell structures such as cell membranes during lyophilization, and thus it is substantially impossible to maintain the function of active ingredients in the cells.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

That is, exosomes called "avatars" of cells contain bioactive factors, such as growth factors, similar to cells. However, when exosomes are stored at room temperature, their stability problems arise that the activity of bioactive factors contained therein is lowered. In addition, when exosomes are simply cold-stored, changes in the overall physical properties and stability of exosomes may occur depending on their storage time and method, and thus the activity of bioactive factors contained therein may also be lowered.

However, although various studies have been conducted, which suggest a possibility for the treatment of some diseases using exosomes, the development of methods which can stably maintain and make exosomes stored, and technologies related to stable exosome formulations has been insufficient. Therefore, there is a need to develop new methods and formulations that make it possible to stably maintain and store exosomes and bioactive factors contained therein.

The present inventors have made efforts to develop a method for lyophilizing exosomes and a cryoprotectant therefor, and as a result, have found that when exosomes are lyophilized with specific saccharides and amino acids under specific conditions, it is possible to obtain a lyophilized product that shows a good appearance which maintains a porous sponge shape without forming ice crystals, thereby completing the present invention.

Meanwhile, it is to be understood that the matters described as the background art are intended merely to aid in the understanding of the background of the present invention and are not admitted as prior art against the present invention.

SUMMARY OF INVENTION

An object of the present invention is to provide a method for lyophilizing exosomes, a cryoprotectant for exosomes, and a composition for lyophilizing exosomes.

Another object of the present invention is to provide lyophilized exosomes or a composition comprising lyophilized exosomes and a diluent, and applications thereof.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a method of lyophilizing exosomes using a cryoprotectant comprising methionine, mannitol and trehalose.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

As used herein, the term "biological solution" refers to a liquid solution having biological origin in which exosomes are dispersed, suspended, precipitated, floated or mixed. Examples of the biological solution include conditioned media of cell cultures, supernatants of cell cultures, conditioned media of stem cell cultures, supernatants of stem cell cultures, whole blood, serum, umbilical cord blood, plasma, ascitic fluids, brain and cerebrospinal fluids, placental extracts, and bone marrow aspirates. However, it is to be understood that the present invention is not limited thereto and does not exclude solutions originating from various organisms, such as various animals, plants, bacteria, fungi, algae, and the like. The biological solution may be cultured or incubated under conditions that release and/or secrete exosomes, and may also be frozen and thawed.

Meanwhile, the term "exosomes" as used herein is intended to include all vesicles (e.g., exosome-like vesicles) which are secreted from the cells of various animals, plants, bacteria, fungi, algae or the like and released into extracellular spaces, and have a nano-sized vesicle structure and a composition similar to that of exosomes.

As an example, not limiting the present invention, the biological solution may be a conditioned medium of stem cell culture. The stem cells are not limited to the kind thereof, but may preferably be mesenchymal stem cells, for example, adipose-, bone marrow-, umbilical cord- or umbilical cord blood-derived stem cells, more preferably adipose-derived stem cells. The adipose-derived stem cells are not limited to the kind thereof as long as they have no risk of infection with pathogens and do not cause immune rejection, but may preferably be human adipose-derived stem cells.

However, exosomes lyophilized according to the present invention are not limited to the above-described exosomes, and it is of course possible to use various exosomes that are being used in the art or may be used in the future. It should be noted that the exosomes isolated according to the isolation method of examples described later should be understood as an example of exosomes that may be used in the present invention, and the present invention is not limited thereto.

A cryoprotectant for exosomes according to one embodiment of the present invention comprises methionine, mannitol and trehalose. The cryoprotectant may be used in the form of an aqueous solution containing methionine, mannitol and trehalose.

In the cryoprotectant for exosomes according to one embodiment of the present invention, the concentration of each of methionine, mannitol and trehalose in the aqueous solution may be in the range of about 5 to 15 mg/mL, preferably about 9 mg/mL.

A composition for lyophilizing exosomes according to one embodiment of the present invention comprises: a cryoprotectant comprising methionine, mannitol and trehalose; and exosomes. The cryoprotectant may be added to an aqueous solution containing ascorbic acid and retinol. The aqueous solution may be water for injection, physiological saline, phosphate buffered saline, purified water, or deionized water.

In the composition for lyophilizing exosomes according to one embodiment of the present invention, the concentration of each of methionine, mannitol and trehalose in the aqueous solution may be in the range of about 5 to 15 mg/mL, preferably about 9 mg/mL. In addition, the concentration of each of ascorbic acid and retinol in the aqueous solution may be, for example, about 0.5 mg/mL.

A method for lyophilizing exosomes according to one embodiment of the present invention comprises the following steps of: (a) preparing exosomes; (b) treating the prepared exosomes with a cryoprotectant comprising methionine, mannitol and trehalose; and (c) lyophilizing the exosomes treated with the cryoprotectant.

In the method for lyophilizing exosomes according to one embodiment of the present invention, step (b) may comprise mixing the exosomes with the cryoprotectant. The cryoprotectant may be added to an aqueous solution containing ascorbic acid and retinol. The aqueous solution may be water for injection, physiological saline, phosphate buffered saline, purified water, or deionized water.

In the method for lyophilizing exosomes according to one embodiment of the present invention, the concentration of each of methionine, mannitol and trehalose in the aqueous solution may be in the range of about 5 to 15 mg/mL, preferably about 9 mg/mL. In addition, the concentration of each of ascorbic acid and retinol in the aqueous solution may be, for example, about 0.5 mg/mL.

In the method for lyophilizing exosomes according to one embodiment of the present invention, step (c) may sequentially comprise: freezing under atmospheric pressure at −50° C. for 10 hours to 15 hours; first drying under vacuum at −50° C. for 50 hours to 60 hours; second drying under vacuum at −20° C. for 1 hour to 3 hours; and third drying under vacuum at 10° C. for 30 minutes to 2 hours.

The present invention also provides a lyophilized formulation of exosomes comprising: as active ingredients, exosomes; and methionine, mannitol, and trehalose. For example, the weight ratio of methionine, mannitol and trehalose in the lyophilized formulation may be 1:1:1.

The lyophilized formulation of exosomes according to one embodiment of the present invention may further comprise ascorbic acid and retinol. For example, the weight ratio of methionine, mannitol, trehalose, ascorbic acid and retinol in the lyophilized formulation may be 9:9:9:0.5:0.5.

The lyophilized formulation of exosomes according to one embodiment of the present invention may be used as a solution obtained by mixing it with a diluent. For example, the diluent may be water for injection, physiological saline, phosphate buffered saline, purified water, or deionized water. In addition, the diluent may further comprise hyaluronic acid or hyaluronate (e.g., sodium hyaluronate).

The lyophilized formulation of exosomes or a composition comprising the same according to one embodiment of the present invention may be a pharmaceutical composition, a cosmetic composition, or a skin external preparation. For example, the lyophilized formulation of exosomes or a composition comprising the same may be prepared as an injectable formulation.

The present invention also provides a suspension of exosomes comprising: lyophilized exosomes as described above; and a diluent. As the diluent, there may be used water for injection, physiological saline, phosphate buffered saline, purified water, deionized water, hyaluronic acid, or the combinations thereof In addition, those known as diluents in the art may be used, including those exemplified later.

The lyophilized exosomes according to one embodiment of the present invention or a composition comprising the same may be prepared as a pharmaceutical composition. When the lyophilized exosomes according to one embodiment of the present invention or a composition comprising the same is prepared as a pharmaceutical composition, the composition according to one embodiment of the present invention may be any formulation for oral or parenteral administration.

The pharmaceutical composition according to one embodiment of the present invention may include pharmaceutically acceptable carriers, excipients, diluents or the like. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. For use, the pharmaceutical composition according to one embodiment of the present invention may be formulated as oral dosage forms, such as powders, pills, tablets, capsules, suspensions, emulsions, syrups, granules, elixirs, aerosols, or the like, skin external preparations, suppositories, or sterile injectable solutions.

Administration of the pharmaceutical composition according to one embodiment of the present invention means introducing a desired substance into a patient by any appropriate method, and the pharmaceutical composition may be administered by any general route, as long as the substance can reach a target tissue. For example, the pharmaceutical composition according to one embodiment of the present invention may be administered orally or parenterally. Routes for parenteral administration may include transdermal administration, intraperitoneal administration, intravenous administration, intra-arterial administration, intralymphatic administration, intramuscular administration, subcutaneous administration, intradermal administration, topical administration, intrarectal administration, and the like. However, the scope of the present invention is not limited thereto, and various administration methods known in the art are not excluded. Furthermore, the pharmaceutical composition according to one embodiment may be administered by any device through which an active ingredient may be delivered into a target tissue or cell. In addition, the effective amount of the pharmaceutical composition according to one embodiment of the present invention means the amount required for administration in order to achieve the effect of treating a disease.

Formulations for parenteral administration of the pharmaceutical composition according to the present invention may be sterilized aqueous solutions, non-aqueous solutions, suspensions, emulsions, lyophilized formulations, or suppositories. Formulations for parenteral administration of the pharmaceutical composition according to one embodiment of the present invention may also be prepared as injectable formulations. Injectable formulations according to one embodiment of the present invention may be aqueous injectable formulations, non-aqueous injectable formulations, aqueous suspension injections, non-aqueous suspension injections, solid injectable formulations which are used after dissolution or suspension, etc., but are not limited thereto.

An injectable formulation according to one embodiment of the present invention may further comprise at least one of distilled water for injection, vegetable oils (e.g., peanut oil, sesame oil, camellia oil, etc.), monoglyceride, diglyceride, propylene glycol, camphor, estradiol benzoate, bismuth subsalicylate, arsenobenzol sodium, or streptomycin sulfate, depending on the type thereof, and may optionally further comprise a stabilizer or a preservative.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the kind of patient's disease, the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Moreover, the present invention is directed to the application of the lyophilized exosomes or the composition comprising the same to a skin external preparation and/or a cosmetic composition. Meanwhile, when the composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation and/or cosmetic composition according to one embodiment of the present invention may comprise, in addition to the lyophilized exosomes according to one embodiment of the present invention or a composition comprising the same, an anti-inflammatory agent and/or a moisturizing agent, which has been used in the prior art, within the range that does not impair the effects (e.g., anti-inflammatory and moisturizing effects) thereof. For example, the lyophilized exosomes or the composition comprising the same of the present invention may be contained in or mixed with at least one of hydrogel, hyaluronic acid, salt of hyaluronic acid (e.g., sodium hyaluronate, etc.), or hyaluronate gel. In the skin external preparation and/or cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

When the skin external preparation according to one embodiment of the present invention is prepared as a cosmetic composition, it is used for the purpose of anti-inflammation, moisturizing, etc., and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

ADVANTAGEOUS EFFECTS

The lyophilized exosomes and the composition comprising the same according to the present invention shows a good appearance which maintains a porous sponge shape without forming ice crystals.

In addition, the lyophilized exosomes and the composition comprising the same according to the present invention can be applied to a pharmaceutical composition, a skin external preparation and a cosmetic composition. For example, the lyophilized exosome product of the present invention can be used as a solution obtained by simply mixing it with a diluent.

It should be understood that the scope of the present invention is not limited to the aforementioned effects.

BRIEF DESCRIPTION OF DRAWINGS

"FIG. 1A" shows the particle size distribution and the number of particles obtained by nanoparticle tracking analysis (NTA). "FIG. 1B" shows particle images obtained by transmitted electron microscopy (TEM)". "FIG. 1C" shows the results of Western blot analysis for positive markers of exosomes obtained according to one embodiment of the present invention. "FIG. 1D" shows the results of Western blot analysis for negative markers of exosomes obtained according to one embodiment of the present invention. "FIG. 1E" shows the results of flow cytometry of CD9, CD63 and CD81 in the analysis of markers for exosomes obtained according to one embodiment of the present invention.

In FIGS. 4 to 7, when RAW 264.7 cells were treated with different concentrations (expressed as the number of particles per mL) of stem cell-derived exosomes (exosomes isolated and purified from conditioned media of stem cells) prepared in Example 2, and then treated with LPS, the LPS-induced production of IL-1β, IL-6, IL-27 and IFN-β in the cells decreased in a manner of depending on the concentration of the exosomes.

In FIGS. 8 to 11, when RAW 264.7 cells were treated with different concentrations (expressed as the number of particles per mL) of aqueous solutions obtained and diluted by mixing a lyophilized formulation of stem cell-derived exosomes (prepared in Example 4-1) with a culture medium, and then treated with LPS, the LPS-induced production of IL-1β, IL-6, IL-27 and IFN-β in the cells remarkably decreased in a manner of depending on the concentration of the lyophilized formulation.

EXAMPLES

Figure 1A:
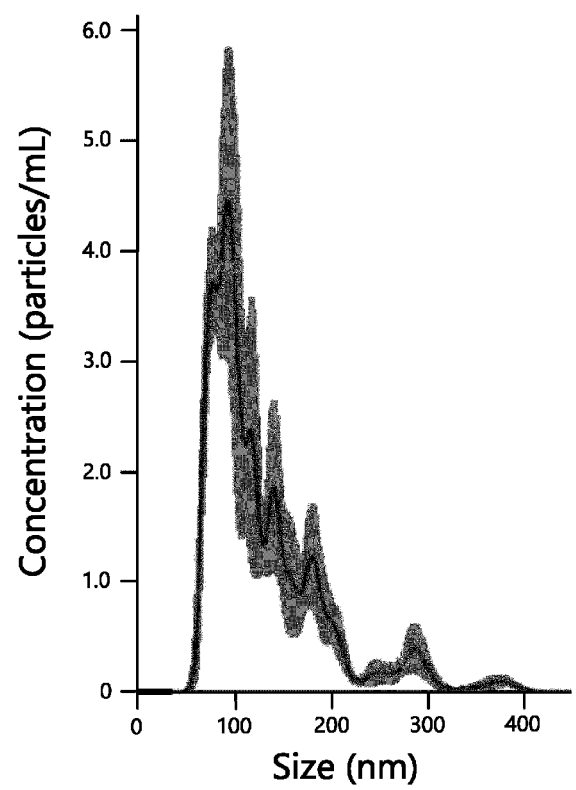
FIGS. 1A to 1E show the results of analyzing the physical properties of exosomes obtained according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by Tangential Flow Filtration (TFF).

Example 2: Isolation and Purification of Exosomes by TFF Method

For isolating, concentrating and diafiltrating exosomes from the conditioned medium filtered through 0.22 μm filter in Example 1, TFF method was used. As a filter for TFF method, a cartridge filter (known as a hollow fiber filter; purchased from GE Healthcare) or a cassette filter (purchased from Pall, Sartorius or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration. The diafiltration was performed continuously (continuous diafiltration) or discontinuously (discontinuous diafiltration), using a buffer having at least 4 times, preferably at least 6 to 10 times, more preferably at least 12 times volume of the starting volume. To obtain exosomes having a uniform particle size distribution and high purity, 2 wt % trehalose in PBS was added to the buffer.

Example 3: Analysis of Characteristics of Isolated Exosomes

Figure 1B:
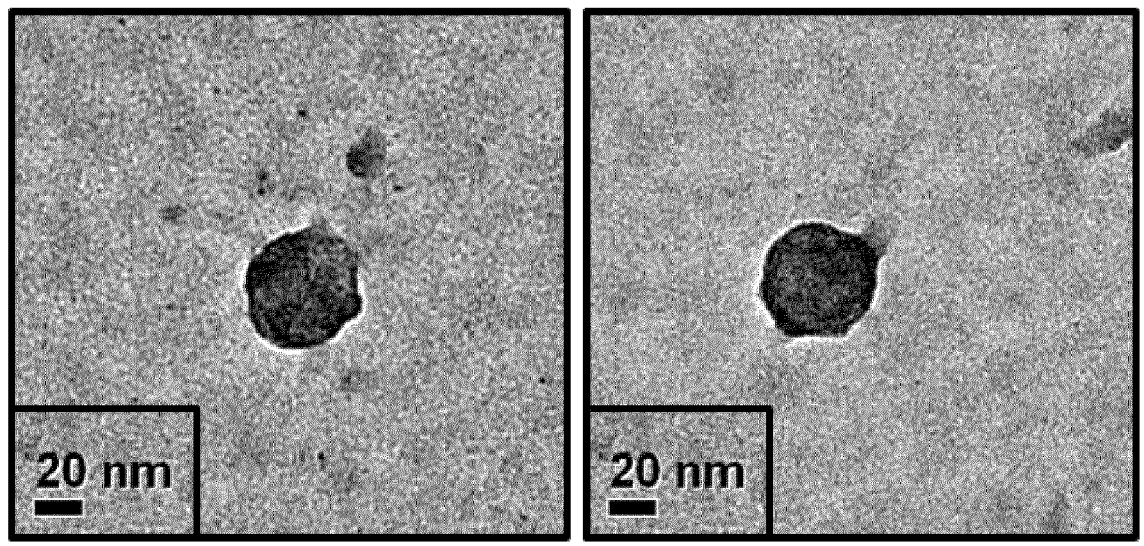

The particle size and concentration of the isolated exosomes were measured by nanoparticle tracking analysis (NTA) instrument (purchased from Malvern). The uniformity and size of the isolated exosomes were analyzed by transmission electron microscopy (TEM). FIGS. 1A and 1B show the results of NTA and TEM of the exosomes isolated by the isolation method according to one embodiment of the present invention.

Figure 1C:
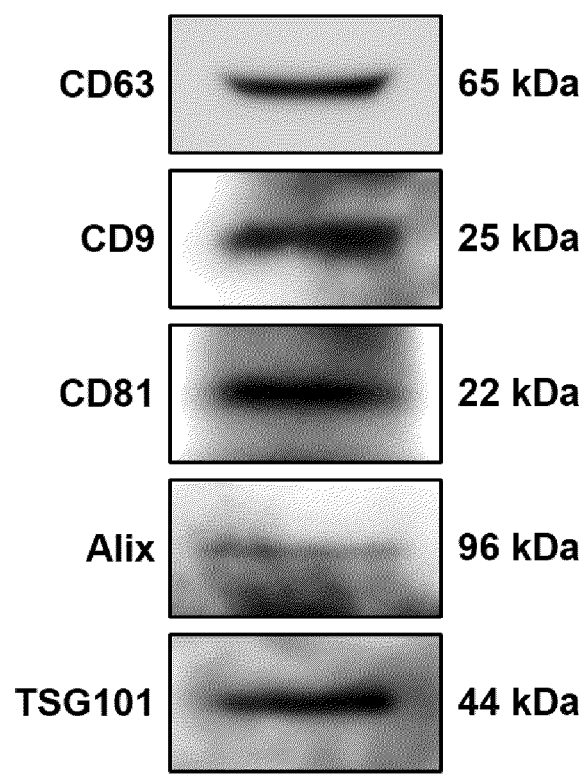

FIG. 1C shows the results of Western blot analysis for positive markers of the exosomes isolated by the isolation method according to one embodiment of the present invention. As shown therein, the presence of CD63, CD9, CD81, Alix and TSG101 markers was confirmed. As antibodies for each of the markers, anti-CD63, anti-CD9, anti-CD81, anti-Alix and anti-TSG101 were used, respectively.

Figure 1D:
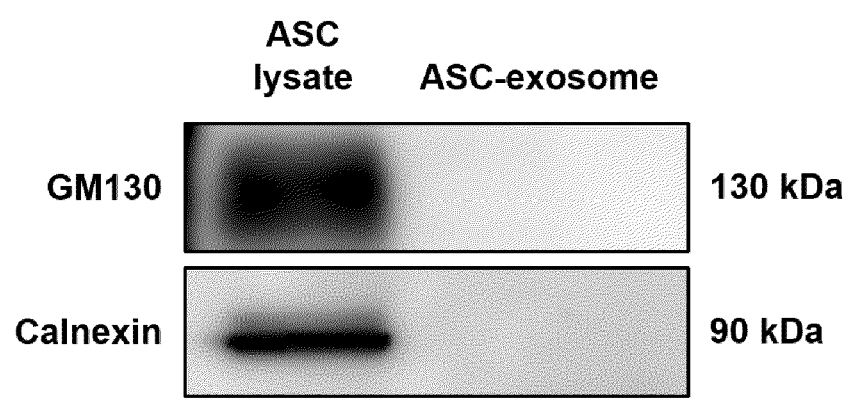

FIG. 1D shows the results of Western blot analysis for negative markers of the exosomes isolated by the isolation method according to one embodiment of the present invention. As antibodies for each of the markers, anti-GM130 and anti-Calnexin were used, respectively. GM130 and Calnexin are negative markers that should not be present in exosomes when the characteristics of the exosomes are analyzed. As shown in FIG. 1D, it was confirmed that GM130 and Calnexin were present in a lysate in adipose-derived stem cells, but were not present in the exosomes isolated by the isolation method according to one embodiment of the present invention. Therefore, when considering the results shown in FIGS. 1C and 1D together, it can be seen that the exosomes isolated by the isolation method according to one embodiment of the present invention are exosomes satisfying the characteristics of the positive markers and negative markers.

Figure 1E:
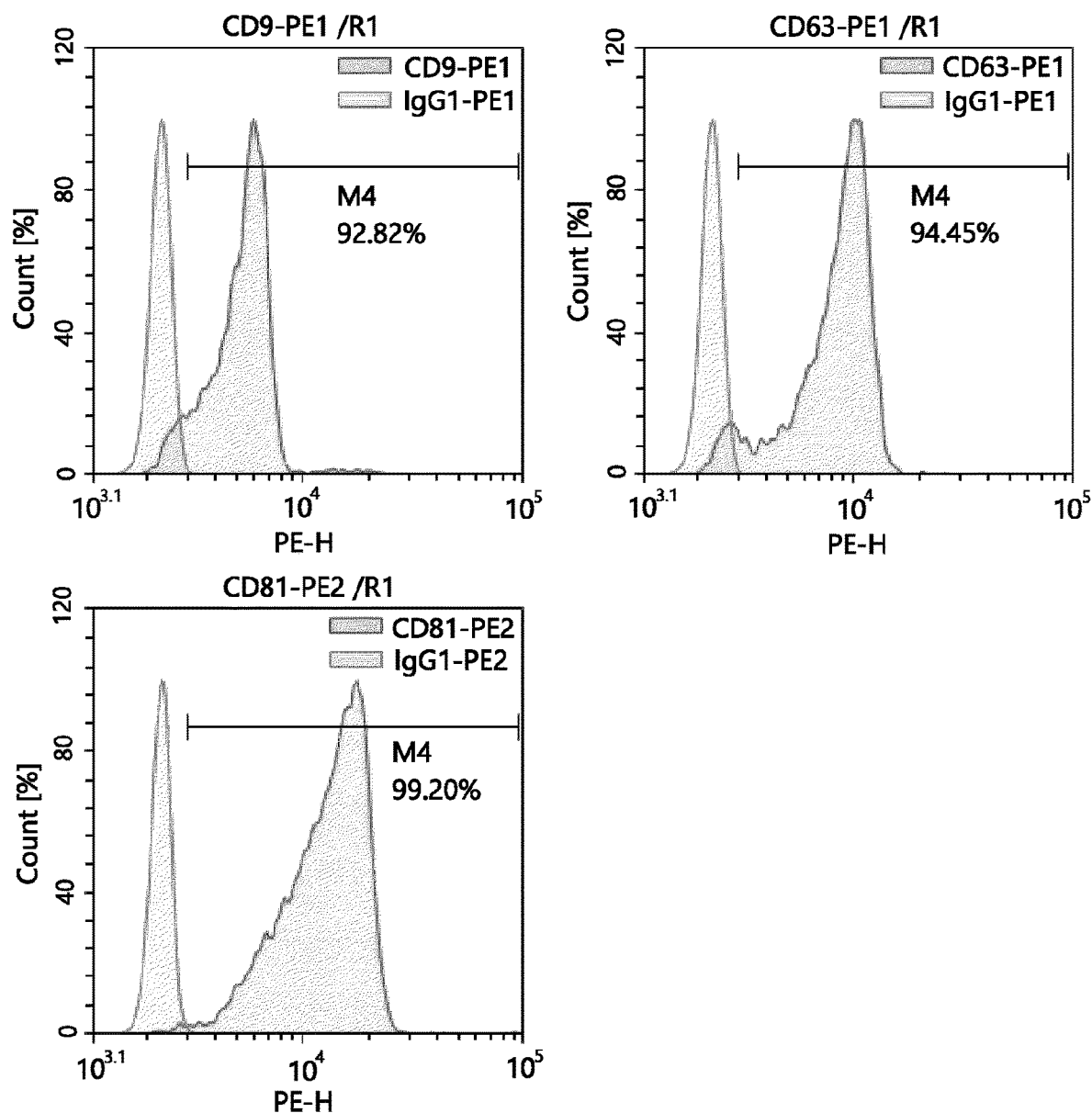

FIG. 1E shows the results of flow cytometry of the exosomes isolated by the isolation method according to one embodiment of the present invention. As shown therein, the presence of CD9, CD63 and CD81 markers was confirmed. To isolate CD81-positive exosomes, an Exosome-Human CD81 Isolation/Detection Reagent kit (purchased from ThermoFisher Scientific) was used according to the manufacturer's instruction. The markers were stained with PE-Mouse anti-human CD9 (purchased from BD), PE-Mouse anti-human CD63 (purchased from BD) or PE-Mouse anti-human CD81 (purchased from BD), and then analyzed using a flow cytometer (ACEA Biosciences).

Meanwhile, it is to be understood that the exosomes that are used in the lyophilizing method of the present invention are not limited to the exosomes of the Examples as described above, it is possible to use various exosomes that are being used in the art or can be used in the future. In addition, it should be noted that the exosomes isolated according to the above Examples should be understood as an example of exosomes that may be used in the lyophilizing method of the present invention, and the scope of the present invention is not limited thereto.

Example 4: Lyophilization of Exosomes

Example 4-1: Lyophilization Conditions

For lyophilization of exosomes, a cryoprotectant comprising methionine, mannitol and trehalose was prepared. An aqueous solution was prepared by adding the cryoprotectant was added to 1 mL of an aqueous solution containing 0.5 mg/mL each of ascorbic acid and retinol (prepared by BIO-FD&C Co., Ltd., Hwasun-gun, Jeollanam-do, Korea). Although the cryoprotectant was added to the solution containing ascorbic acid and retinol in this Example, an aqueous solution may also be prepared by adding the cryoprotectant to water for injection, purified water, physical saline, or deionized water. The concentration of each of methionine, mannitol and trehalose in the aqueous solution was adjusted to 9 mg/mL.

The exosomes ($5 \times 10^8$ particles/mL) prepared in Example 2 were mixed with the aqueous solution containing the cryoprotectant, and then lyophilized using a lyophilization system (manufactured by VIRTIS, ITEM No.: 344424) under the conditions shown in Table 1 below. The lyophilization was performed in the order of conditions 1, 2, 3, 4, 5, 6, 7 and 8 as shown in Table 1 below.

TABLE 1

| Lyophilization conditions | | | |
| --- | --- | --- | --- |
| Total time (min) | | 4320 | |
| Conditions | Time (min) | Temperature (° C.) | Pressure (mmHg) |
| 1 | 700 | −50 | 760 |
| 2 | 60 | −50 | 760 |
| 3 | 999 | −50 | 0 |

TABLE 1-continued

Lyophilization conditions

Total time (min) 4320

| Conditions | Time (min) | Temperature (° C.) | Pressure (mmHg) |
|---|---|---|---|
| 4 | 999 | −50 | 0 |
| 5 | 999 | −50 | 0 |
| 6 | 370 | −50 | 0 |
| 7 | 120 | −20 | 0 |
| 8 | 73 | 10 | 0 |

Figure 2:
FIG. 2 depicts a photograph showing a good appearance of exosomes lyophilized according to one embodiment of the present invention.

After the exosomes were treated with the cryoprotectant comprising methionine, mannitol and trehalose, and lyophilized, the appearance thereof was examined. As a result, it can be seen that the exosomes were milky white in color and showed a good appearance which maintains a porous sponge shape (FIG. 2). That is, the method for lyophilizing exosomes according to the present invention is able to produce a lyophilized product having a good appearance by prolonging the drying time under vacuum and using the cryoprotectant having the combination of methionine, mannitol and trehalose.

Example 4-2: Comparison of Appearances of Lyophilized Exosomes Depending on Cryoprotectant Components Meanwhile, the appearances of exosomes lyophilized using various cryoprotectants comprising at least one of methionine, mannitol and trehalose (hereinafter, referred to as cryoprotectant components) were compared. According to the method described in Example 4-1 above, seven different aqueous solutions were prepared by adding the cryoprotectant components alone, combinations of two components, or a combination of three components. The concentration of each of the cryoprotectant components in each of the aqueous solutions was adjusted to 9 mg/mL. According to the lyophilization conditions and method described in Example 4-1 above, the exosomes ($5 \times 10^8$ particles) prepared in Example 2 above were mixed with the respective aqueous solution containing each of the cryoprotectant components alone, each of the combinations of two components, or the combination of three components, and then lyophilized.

The external appearances of the lyophilized exosome products were photographed and evaluated (FIGS. 3A to 3G). According to the states of the cake shapes of the lyophilized exosome products, the appearances of the lyophilized exosome products were ranked and relatively evaluated in a 5-point scale ranging from 1 (the worst cake appearance) to 5 (the best cake appearance). Table 2 below shows the results of evaluating the appearances of the lyophilized exosome products according to the combinations of the cryoprotectant components.

TABLE 2

Comparison of appearances of lyophilized exosome products according to combinations of cryoprotectant components

Figure 3A:
FIGS. 3A to 3G are photographs each of which shows, after performing lyophilization using different combinations of cryoprotectant components, the appearance of lyophilized exosomes obtained according to each of the combinations of cryoprotectant components.
Figure 3B:
Figure 3C:
Figure 3D:
Figure 3E:
Figure 3F:
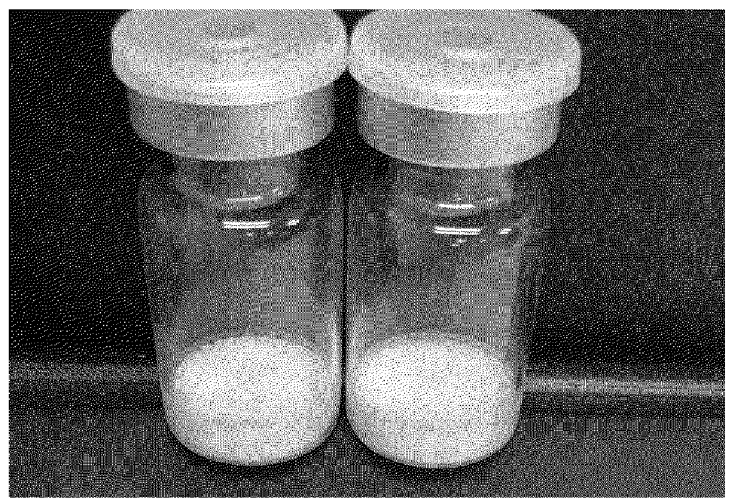
Figure 3G:
Figure 4:
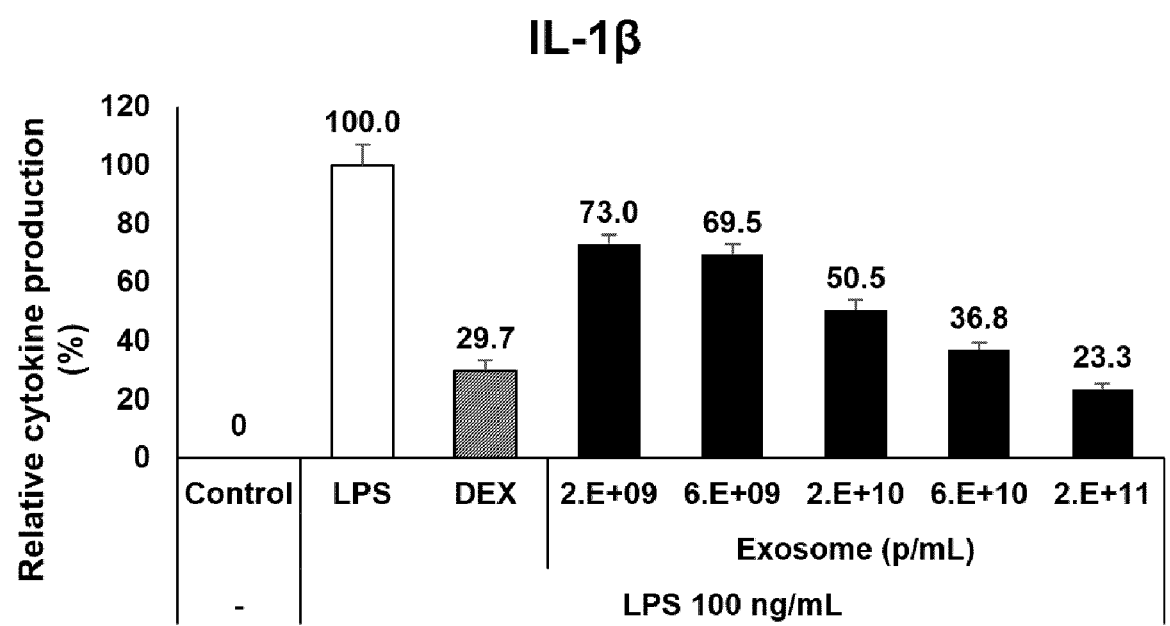
FIGS. 4 to 7 show the results of analyzing inflammatory cytokines using a multiplex panel.
Figure 5:
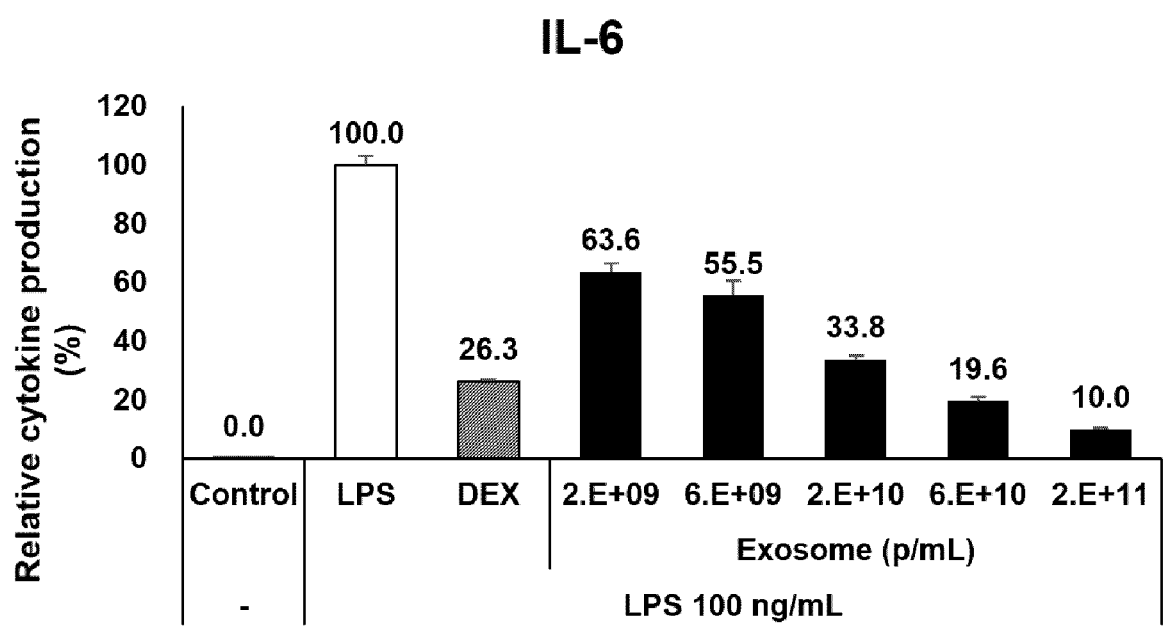
Figure 6:
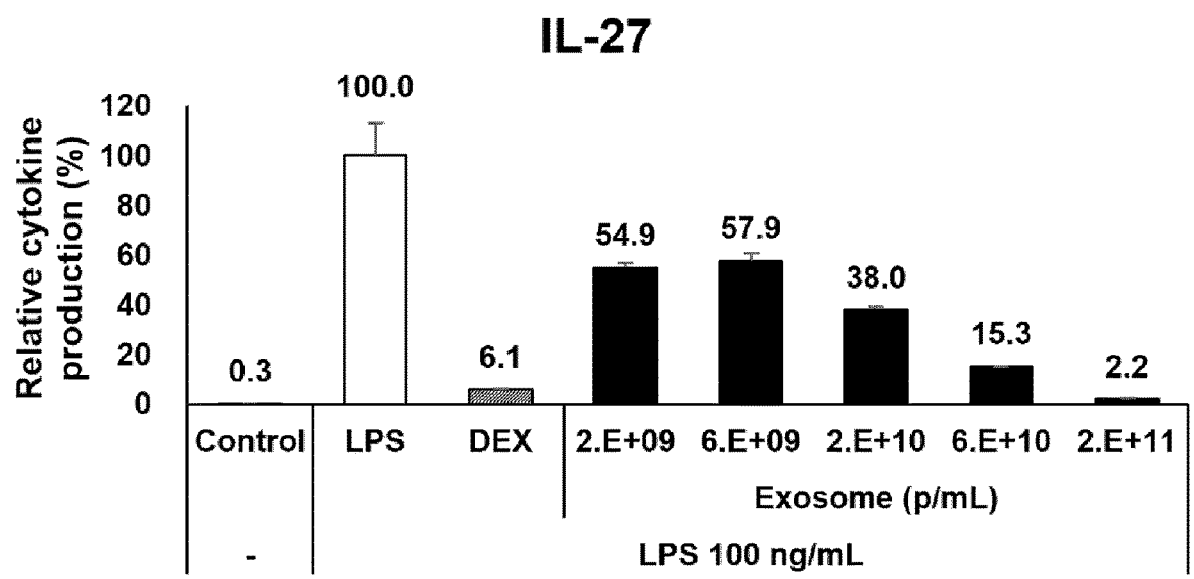
Figure 7:
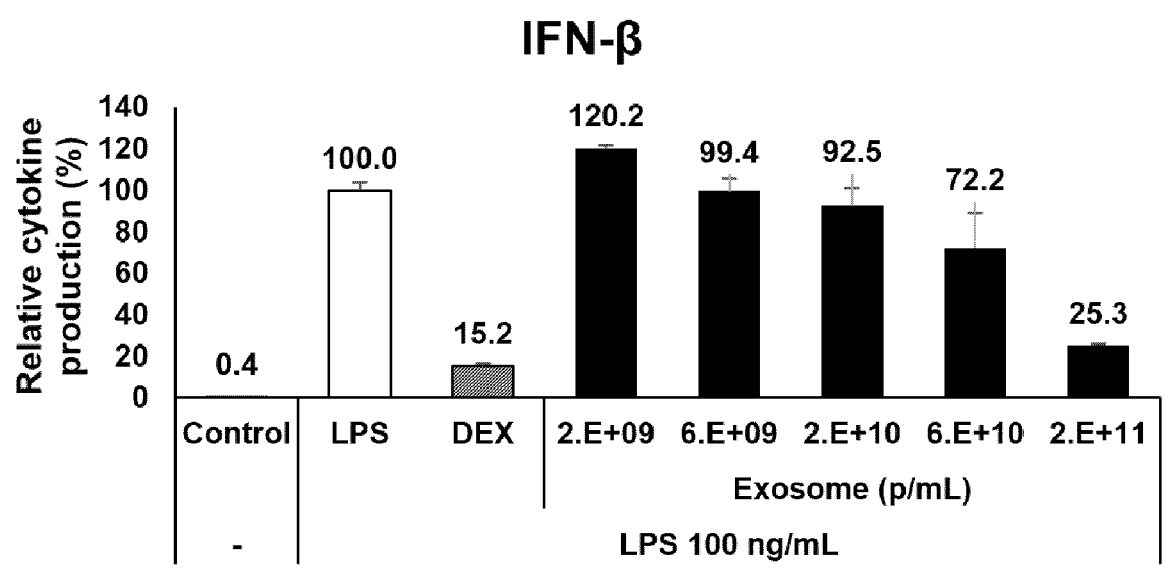
Figure 8:
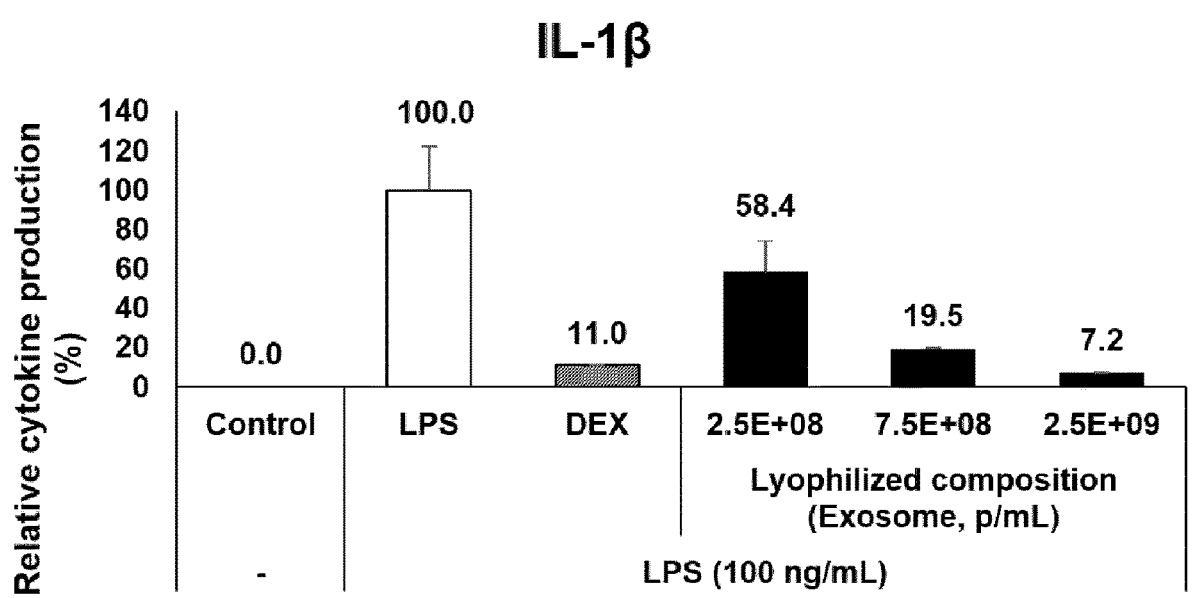
FIGS. 8 to 11 show the results of analyzing inflammatory cytokines using a multiplex panel.
Figure 9:
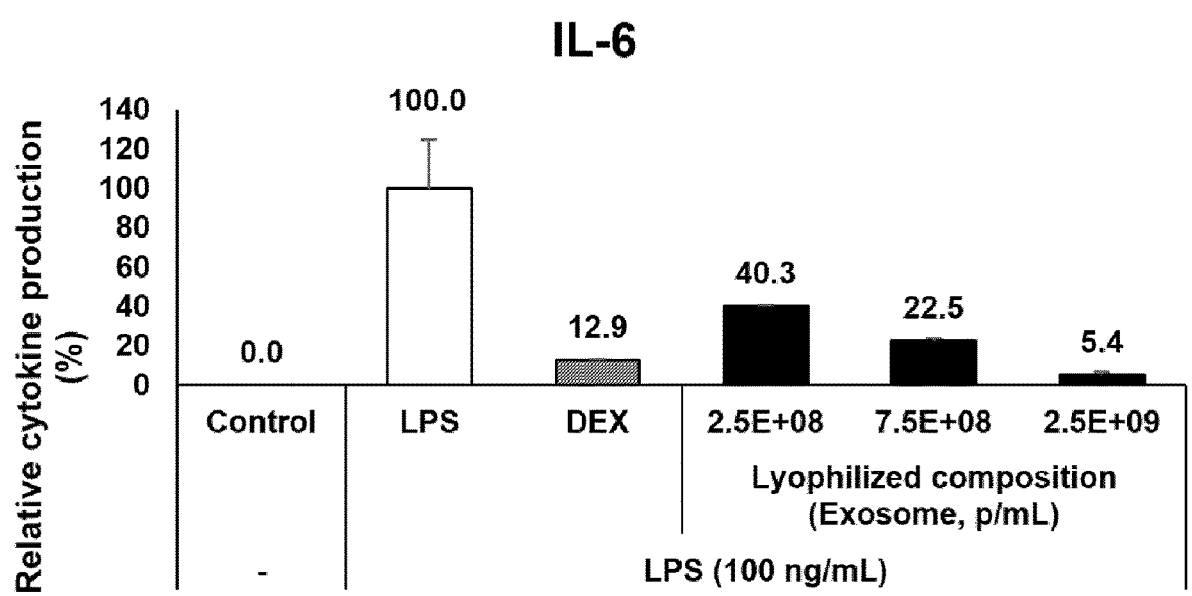
Figure 10:
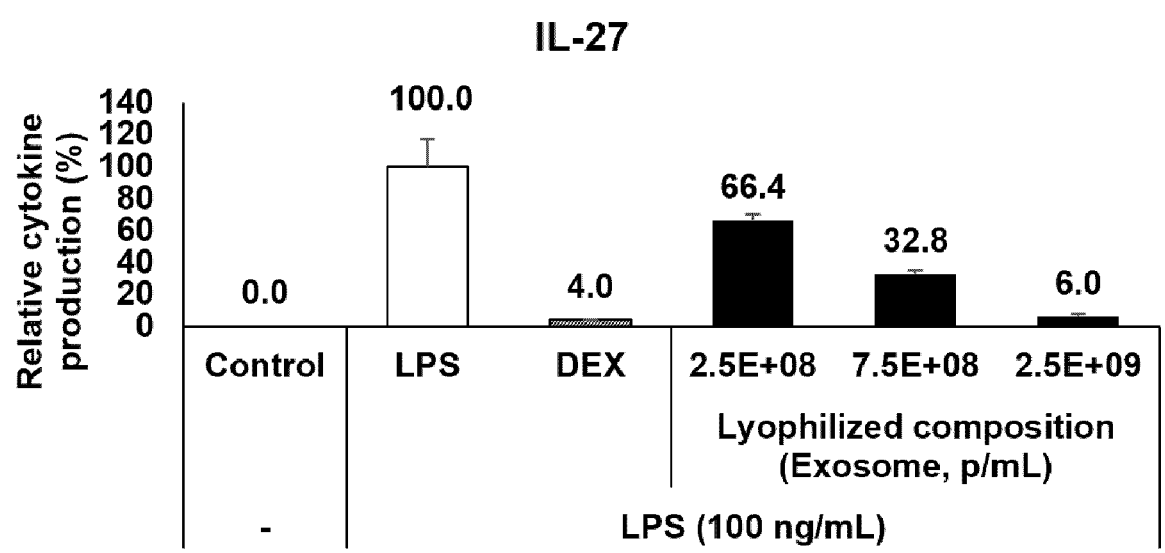
Figure 11:
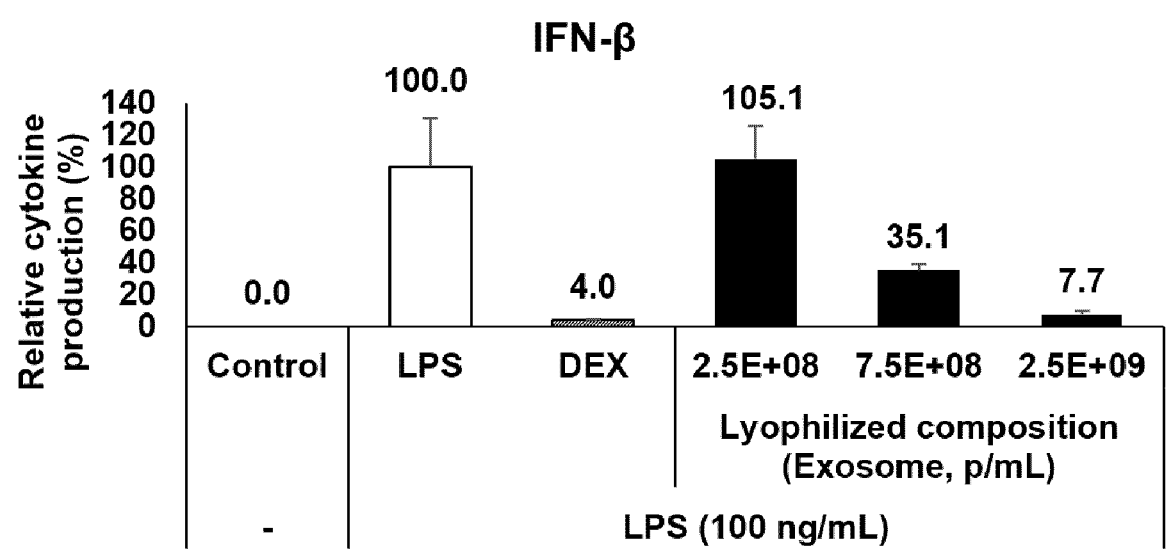

| | Composition of cryoprotectant components | | | | | | |
|---|---|---|---|---|---|---|---|
| | Mannitol | Trehalose | Methionine | Methionine + trehalose | Methionine + mannitol | Trehalose + mannitol | Methionine + mannitol + trehalose (present invention) |
| Evaluated score | 1 | 1 | 4 | 3 | 4 | 2 | 5 |
| FIGS. | FIG. 3A | FIG. 3B | FIG. 3C | FIG. 3D | FIG. 3E | FIG. 3F | FIG. 3G |

As shown in FIGS. 3A to 3G and Table 2 above, it can be seen that the product obtained by lyophilizing exosomes using the cryoprotectant having the combination of methionine, mannitol and trehalose has the best external appearance, however, the external appearances of the products obtained by lyophilizing exosomes using the one component or the combinations of the two components are poorer than that of the product of the present invention.

Example 5: Evaluation of Effect of Decreasing Inflammatory Cytokine Production The effects of stem cell-derived exosomes (Example 2) and the lyophilized formulation (Example 4-1) of stem cell-derived exosomes upon decreases in inflammatory cytokine production in mouse macrophage RAW 264.7 cells were evaluated as follows.

RAW 264.7 cells were suspended in DMEM (Dulbecco Modified Eagle Medium; purchased from ThermoFisher Scientific) containing 10% FBS (Fetal Bovine Serum) and 1% penicillin-streptomycin, and then seeded into a 96-well plate at a density of $2.5 \times 10^4$ cells/well. Next, the cells were treated with difference concentrations (expressed as the number of particles per mL) of stem cell-derived exosomes (exosomes isolated and purified from conditioned media of stem cells) prepared in Example 2, and then cultured in an incubator at 37° C. under 5% $CO_2$ for 24 hours. In addition, in the same manner as the above-described method of treatment with stem cell-derived exosomes, RAW 264.7 cells were treated with aqueous solutions obtained and diluted by mixing the lyophilized formulation of stem cell-derived exosomes ($5 \times 10^9$ particles/vial) of Example 4-1 with a culture medium, and then the treated RAW 264.7 cells were cultured in an incubator at 37° C. under 5% $CO_2$ for 24 hours. Meanwhile, as a positive control, dexamethasone was used (indicated as DEX in FIGS. 4 to 11).

Thereafter, the RAW 264.7 cells were treated with 100 ng/mL of LPS (purchased from Sigma), and cultured in an incubator at 37° C. under 5% $CO_2$ for 24 hours, thus inducing activation of the cells.

After completion of the culture, the culture supernatant of the RAW 264.7 cells was collected, and the production of IL-1β, IL-6, IL-27 and IFN-β in the culture supernatant was measured using a mouse inflammation panel for LEGEND-plex™ bead-based immunoassay (purchased from Biolegend) and NovoCyte Flow Cytometer (purchased from ACEA) in order to evaluate anti-inflammatory effects.

In addition, an MTT assay was performed to measure the change in cell viability caused by stem cell-derived exosomes, and the lyophilized formulation of stem cell-derived exosomes of the present invention, respectively, and to normalize the cytokine production therethrough. After the completion of culture, the culture medium of the RAW 264.7 cells was replaced with a DMEM medium containing 0.5 mg/mL of thiazolyl blue tetrazolium bromide (purchased from Sigma) and cultured for 1 hour. Next, the supernatant was removed in such a manner that the formazan formed at the bottom of the cell culture plate was not scattered. Subsequently, the formazan was dissolved by dimethyl sulfoxide (purchased from AMRESCO), and the absorbance was measured at 570 nm to determine the cell viability. In addition, the production of each of cytokines (IL-1β, IL-6, IL-27 and IFN-β) was normalized by the cell viability.

As shown in FIGS. 4 to 7, from the results of analyzing the inflammatory cytokines using the multiplex panel, it can be seen that when the RAW 264.7 cells were treated with the stem cell-derived exosomes before treating the cells with LPS, the LPS-induced production of each of IL-1β, IL-6, IL-27 and IFN-β decreased in a manner of depending on the concentration of the exosomes. In addition, as shown in FIGS. 8 to 11, from the results of analyzing the inflammatory cytokines using the multiplex panel, it can be seen that when the RAW 264.7 cells were treated with the lyophilized formulation of stem cell-derived exosomes before treating the cells with LPS, the LPS-induced production of each of IL-1β, IL-6, IL-27 and IFN-β remarkably decreased in a manner of depending on the concentration of the lyophilized formulation.

From these results, it can be seen that the lyophilized formulation of stem cell-derived exosomes according to the present invention is able to stably maintain the anti-inflammatory efficacy of stem cell-derived exosomes contained therein as an active ingredient, and thus there is no possible change in the physical properties of exosomes during lyophilization, storage and distribution. Therefore, the lyophilized formulation of stem cell-derived exosomes according to the present invention is able to stabilize exosomes and make them commercially useful.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A composition for lyophilizing exosomes comprising:
   an aqueous solution prepared by adding a cryoprotectant to an aqueous solution containing ascorbic acid and retinol, wherein the cryoprotectant comprises methionine, mannitol and trehalose; and
   exosomes.

2. A method for lyophilizing exosomes, the method comprising the following steps of:
   (a) providing exosomes;
   (b) treating the exosomes with a cryoprotectant comprising methionine, mannitol, trehalose, ascorbic acid and retinol; and
   (c) lyophilizing the exosomes treated with the cryoprotectant;
   wherein step (b) comprises mixing the exosomes with the cryoprotectant.

3. A method for lyophilizing exosomes, the method comprising the following steps of:
   (a) providing exosomes;
   (b) treating the exosomes with a cryoprotectant comprising methionine, mannitol, trehalose, ascorbic acid and retinol; and
   (c) lyophilizing the exosomes treated with the cryoprotectant;
   wherein step (c) sequentially comprises:
   freezing under atmospheric pressure at −50° C. for 10 hours to 15 hours;
   first drying under vacuum at −50° C. for 50 hours to 60 hours;
   second drying under vacuum at −20° C. for 1 hour to 3 hours; and
   third drying under vacuum at 10° C. for 30 minutes to 2 hours.

4. A lyophilized formulation of exosomes comprising as active ingredients, exosomes; and methionine, mannitol, trehalose, ascorbic acid and retinol.

5. A composition comprising the lyophilized formulation according to claim 4.

6. The composition of claim 5, wherein the composition is a pharmaceutical composition prepared as an injectable formulation.

7. The composition of claim 5, wherein the composition is a cosmetic composition.

8. The composition of claim 5, wherein the composition is a skin external preparation.

9. A lyophilized formulation of exosomes comprising as active ingredients, exosomes; and methionine, mannitol, trehalose, ascorbic acid and retinol;
   wherein the lyophilized formulation is used as a solution obtained by mixing the lyophilized formulation with a diluent;
   wherein the diluent is water for injection, physiological saline, phosphate buffered saline, purified water, or deionized water; and
   wherein the diluent further comprises hyaluronic acid or hyaluronate.

* * * * *